United States Patent [19]

Newallis et al.

[11] Patent Number: 4,978,795
[45] Date of Patent: Dec. 18, 1990

[54] METHOD TO PREPARE TRIMETHYLSULFONIUM HALIDES

[75] Inventors: Peter E. Newallis, LeaWood, Kans.; Jeffrey D. Macke, Kansas City, Mo.; Karl G. Steinbeck, LeaWood, Kans.; Daniel N. Wasleski, Raytown, Mo.

[73] Assignee: Mobay Corporation, Pittsburgh, Pa.

[21] Appl. No.: 321,600

[22] Filed: Mar. 10, 1989

[51] Int. Cl.$^5$ .............................................. C07C 319/20
[52] U.S. Cl. ........................................................ 568/56
[58] Field of Search ........................................... 568/56

[56] References Cited

U.S. PATENT DOCUMENTS

| 3,101,265 | 8/1963 | Smutny et al. | 71/66 |
| 4,743,403 | 5/1988 | Nagubandi | 568/74 |

OTHER PUBLICATIONS

Andreas Merz et al., Angew. Chem. Internat. Edition, vol. 12, pp. 845–846, 1973, Phase-Transfer-Catalyzed Production of Sulfur Ylides.

Melvin J. Hatch, Journal of Organic Chem., vol. 34, pp. 2133–2137, 1969, The Synthesis of Oxiranes From Aqueous Solutions . . . .

Yasuichiro Shiraki et al., The Chemical Society of Japan, 1985, pp. 3041–3042, Anion-Catalyzed Phase--Transfer . . . .

Primary Examiner—Mary E. Ceperley
Attorney, Agent, or Firm—Joseph C. Gil; Lyndanne M. Whalen

[57] ABSTRACT

Trimethylsulfonium halides are made by reacting dimethyl sulfide and a methyl halide in the presence of water. The reaction is preferably conducted under pressure.

9 Claims, No Drawings

METHOD TO PREPARE TRIMETHYLSULFONIUM HALIDES

BACKGROUND OF THE INVENTION

The present invention relates to an improved process for the production of trimethylsulfonium halides useful for producing oxiranes.

Trimethylsulfonium halides are useful precursors for epoxidation via sulfur ylides to form oxiranes. The use of aqueous trimethylsulfonium halides in phase transfer catalyst reactions with carbonyl compounds is known. See, for example, Merz et al. *Angew. Chem. Internat. Edit.*, Vol. 12, pp. 845-6 (1973) and Hatch, *J. Org. Chem.* Vol 34, pp. 2133-2137 (1969). However, these aqueous solutions are formed by dissolving preformed trimethylsulfonium halides in water. The trimethylsulfonium halides are typically formed by reacting dimethyl sulfide and methyl halides in an organic polar solvent such as methanol or ethanol. The organic solvent must be completely removed before the trimethylsulfonium halide is added to the epoxidation mixture because the organic solvent will degrade the ylide.

It would therefore be advantageous to produce trimethylsulfonium halides directly in water so that the resulting aqueous solution could be used directly in the epoxidation process. Such a process would decrease the cost of making such intermediates because organic solvents would not be required, handling of the salt would be much easier and the need to purify the salt form organic impurities would be eliminated.

SUMMARY OF THE INVENTION

It is an object of the present invention to provide a process for producing trimethylsulfonium halides in water rather than an organic solvent.

These and other objects which will be apparent to those skilled in the art are accomplished by reacting dimethyl sulfide and a methyl halide in the presence of water, preferably under pressure. The resultant trimethylsulfonium halide containing aqueous solution may then be reacted directly with a carbonyl compound to produce an oxirane. The aqueous trimethylsulfonium halide solution may also be subjected to a process such as azeotropic distillation to remove the water if the trimethylsulfonium halide salt in solid form is desired.

DETAILED DESCRIPTION OF THE INVENTION

The present invention relates to an improved process for producing trimethylsulfonium halides in which water is the solvent. The resultant aqueous trimethylsulfonium halide solutions may be used either directly or after treatment (e.g., to remove water) to produce oxiranes by techniques known to those skilled in the art.

In the present invention, dimethyl sulfide is reacted with a methyl halide in the presence of water. Any methyl halide may be used but methyl chloride and methyl bromide are preferred. Water alone is the most preferred solvent but mixtures of water and an organic solvent such as toluene may also be used. Water-miscible systems composed of water and an organic solvent which is miscible in water (e.g. methanol) may also be used as the solvent. Water-immiscible systems composed of water and an organic solvent which is immiscible in water (e.g. toluene) may also be used as the solvent in the process of the present invention. Combinations of water-miscible and water-immiscible systems (e.g. water, methanol and toluene) may, of course, also be used.

Examples of appropriate water-miscible solvents include: methanol, ethanol and tetrahydrofuran. Examples of appropriate water-immiscible solvent include: toluene, xylenes and methylene chloride.

When an organic co-solvent is used in combination with water in the practice of the present invention, the specific amount of water present has not been found to be critical to obtaining the desired trimethylsulfonium halide. However, in order to obtain the full advantage of using water as the solvent it is preferred that at least 5% of any solvent combination be water, more preferably at least 60% water and most preferably, at least 80% water.

A catalyst may also be employed in the process of the present invention, Examples of suitable catalysts include: sodium iodide, potassium iodide and cesium iodide.

Either the dimethylsulfide or the methyl halide may be used in a stoichiometric excess. Which reactant is used in excess is determined by the physical handling characteristics of the mixture and the cost of the reactants and equipment rather than any limitation due to the reaction itself.

For example, methyl chloride is the cheapest of the methyl halides and could therefore be used in excess without making the process economically prohibitive. However, if methyl bromide is selected as the methyl halide, it is desirable to use an excess of dimethyl sulfide because dimethyl sulfide has the higher of the two boiling points (i.e., 37° C.) and may be readily recovered. Methyl iodide is the most expensive of the readily available methyl halides and would not therefore be used in excess in a commercial process for economic reasons, if it were used at all.

The temperature and pressure at which the process of the present invention is conducted are not limited by the chemistry of the reaction. High temperatures and/or pressures do increase the reaction rate but they also require more expensive equipment. Lower pressures are therefore generally preferred because readily available and less expensive equipment may be employed.

The reaction is generally carried out under pressure, preferably under pressure of up to 80 psig, most preferably under pressure of up to 50 psig. The reaction temperatures generally range from 50° to 70° C., preferably from 55° to 60° C. The reaction time may range from 3 to 6 hours, preferably from 4 to 5 hours.

The aqueous trimethylsulfonium halide solution may then be used directly in any of the known processes for producing oxiranes. One such known process is disclosed by Hatch in his article "The Synthesis of Oxiranes from Aqueous Solutions of Simply Alkyl, Allyl, and Benzylsulfonium Salts" published in Vol. 34 of *The Journal of Organic Chemistry* at pages 2133-2137 (July 1969). Other examples of processes for producing oxiranes from trimethylsulfonium halides are discussed in Shiraki et al "Anion-Catalyzed Phase-Transfer Catalysis II. Effects of Anionic Tetrakis[3,5-bistrifluoromethyl)phenyl] borate Catalyst in Phase-Transfer-Catalyzed Sulfonium Ylide Formation", *Bull. Chem. Soc. Jpn.*, 58, 3041-3042 (1985) and Merz et al. "Phase-transfercatalyzed Production of Sulfur Ylides in an Aqueous System," *Angew. Chem. Internat. Edit.* 12, pages 845-846 (1973).

Having thus described our invention, the following examples are given to illustrate the invention.

EXAMPLES

Example 1

124 grams of dimethyl sulfide and 150 ml of water were charged to a reaction vessel. 102 grams of methyl chloride were then charged to the vessel over a period of 13 hours. The mixture was then heated to a temperature of 58°-60° C. and maintained at that temperature under a pressure of 80 psig for four hours. 115.3 grams of trimethylsulfonium chloride (51.2% yield) were isolated from the reaction mixture.

Example 2

148.4 grams of dimethyl sulfide, 100 ml of water and 278 grams of methyl bromide were reacted at a temperature of 58°-60° C. under a pressure of 60 psig for about 3 hours at which time the pressure dropped to about 45 psig where it was maintained for three hours. 365.5 grams of trimethylsulfonium bromide (i.e., a 97.5% yield) were isolated from the reaction mixture.

Example 3

136.4 grams of dimethyl sulfide, 202.0 grams of methyl bromide and 100 ml of water were reacted at 61° C. under a pressure of 50 psig for about one hour. The pressure then dropped to 40 psig and the mixture was heated to 65°-67° C. to maintain the pressure at about 40 psig for about 3 hours. Heating was then discontinued and 335.9 grams of trimethylsulfonium bromide (100.4%) yield based on methyl bromide and 97.3% based on dimethylsulfide) were isolated from the reaction mixture.

Example 4

136.4 grams of dimethylsulfide, 224 grams of methyl bromide and 100 ml of water were charged to a reactor and heated at a temperature of 60° C. and pressure of 60 psig. The temperature was then increased to 70° C. where it was maintained for 2 hours.

The reaction mixture was placed in another vessel heated by an oil bath. 500 ml of toluene were added. A toluene-water azeotropic was distilled off at 90°-98° C. while the toluene and water were being removed, 600 ml mole of toluene were added. Salt started to cake on the wall of the distillation vessel after about 65 ml of water had been removed. 323.1 grams of trimethylsulfonium bromide (93.5% yield) were obtained.

Example 5

100 ml methanol, 5.0 grams of sodium iodide, 103.6 grams of methyl chloride and 124 grams of dimethyl sulfide were reacted at 59° C. under a pressure of 72 psig for 17 hours. The yield of trimethylsulfonium chloride was 74.3%.

Example 6

46.5 grams (0.75 mole) of dimethyl sulfide, 94 grams (1 mole) of methyl bromide and various amounts of water and indicated co-solvents were reacted at 60°-70° C. under a pressure of 50-800 psig for the time indicated. The variables and results of these reactions are indicated in Table I.

TABLE I

| Example | Water (ml) | Add Time (hours) | Comments | Crude Yield (%) | Active Ingredient (%) | Net Yield (%) |
|---|---|---|---|---|---|---|
| A | 50 | 4.0 | ON/recharge 20% MeBr | 61.0 | 98.8 | 60.2 |
| B | 200 | 6.0 | ON/recharge 10% MeBr | 85.1 | 99.0 | 84.2 |
| C | 200 | 4.0 | 10 ml DEG/ON | 90.4 | 93.3 | 84.3 |
| D | 50 | 4.5 | ON | 95.0 | 99.1 | 94.2 |
| E | 100 | 4.0 | 100 g MeOH 2 hr cook/ON (not necessary) | 98.7 | 99.2 | 97.9 |
| F | 100 | 4.5 | 100 g toluene/ 3 × ON (approx 22 hrs @ 60° C.) | 97.0 | 98.2 | 95.3 |
| G | 200 | 4.0 | ON | 94.3 | 99.4 | 93.8 |
| H | 150 | 4.5 | 50 g MeOH/ON | 95.0 | 98.5 | 93.6 |

MeBr = methyl bromide
ON = overnight
DEG = diethylene glycol
MeOH = methanol

Example 7

46.5 grams of dimethyl sulfide, the indicated amounts of methyl chloride and water were reacted at the temperatures and pressures indicated in Table II for the specified amount of time. Examples N, O and P given in Table II were done at low pressure by opening the cylinder of methyl chloride (59 psi) and allowing the cylinder pressure to govern the pressure in the reactor. Back flow was controlled by a one pound check valve. There was no post cook period during these runs.

TABLE II

| | TRIMETHYLSULFONIUM CHLORIDE | | | | | | |
|---|---|---|---|---|---|---|---|
| Example | Time | MeCl | Temp H$_2$O (°C.) | Psi | Max Yield (%) | Active Ingredient (%) | Net Yield (%) |
| I | 20 hr | 200 g | 85 | 310 | 85 | 99.5 | 85 |
| J | 4 hr | 50 g | 85 | 220 | 84 | 100.7 | 85 |
| K | 2 hr | 27 g | 85 | 220 | 79 | 100.3 | 79 |
| L | 20 hr | 50 g | 65 | 150 | 92 | 100.2 | 92 |
| M | 4 hr | 10 g | 65 | 120 | 37 | 100.2 | 37 |
| N | Check Valve | (−10) | 70[1] | 75[2] | 60 | 100.4 | 60 |
| O | Check Valve | (10) | 45–50[3] | 80[4] | 25 | 99.4 | 25 |

TABLE II-continued

| | | TRIMETHYLSULFONIUM CHLORIDE | | | | | |
|---|---|---|---|---|---|---|---|
| Example | Time | MeCl | Temp H$_2$O (°C.) | Psi | Max Yield (%) | Active Ingredient (%) | Net Yield (%) |
| P | Check Valve | 6 | 55 | 75 | 74 | 96.6[5] | 72 |

[1] Init 88° C.
[2] 70 psi 80% of time
[3] Init 75° C.
[4] 70 psi 90% of time
[5] 5% NaI initial Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a trimethylsulfonium halide comprising reacting dimethyl sulfide and a methyl halide in the presence of a solvent which solvent is at least 60% water under pressure at a temperature of from about 45° to about 85° C.

2. The process of claim 1 in which the reaction is carried out at a pressure of up to 80 psig.

3. The process of claim 2 in which the methyl halide is methyl chloride.

4. The process of claim 2 in which the methyl halide is methyl bromide.

5. The process of claim 1 in which the methyl halide is methyl chloride.

6. The process of claim 1 in which the methyl halide is methyl bromide.

7. The process of claim 1 in which a water-miscible solvent is included in the solvent.

8. The process of claim 7 in which a water-immiscible solvent is included in the solvent.

9. The process of claim 1 in which a water-immiscible solvent is included in the solvent.

* * * * *